United States Patent
Guillaume et al.

(10) Patent No.: US 7,059,795 B2
(45) Date of Patent: *Jun. 13, 2006

(54) CONTAINER FOR DISPENSING A HEATED FLUID

(75) Inventors: Bruno Guillaume, Prunay en Yvelines (FR); Bruno Lablaine, Cintray (FR); Serge Ruello, Luisant (FR)

(73) Assignee: Reckitt Benckiser France, Cedex (FR)

( * ) Notice: Subject to any disclaimer, the term of this patent is extended or adjusted under 35 U.S.C. 154(b) by 382 days.

This patent is subject to a terminal disclaimer.

(21) Appl. No.: 10/613,952

(22) Filed: Jul. 3, 2003

(65) Prior Publication Data

US 2005/0254878 A1     Nov. 17, 2005

Related U.S. Application Data

(62) Division of application No. 09/937,050, filed on Sep. 20, 2001, now Pat. No. 6,616,363.

(30) Foreign Application Priority Data

Mar. 19, 1999   (EP)   ................................ 99400667
Jun. 10, 1999   (GB)   ................................ 9913461.1

(51) Int. Cl.
   *A46B 11/08*     (2006.01)
   *B05C 17/00*     (2006.01)
   *B05C 21/00*     (2006.01)

(52) U.S. Cl. ........................... 401/1; 401/208; 401/196
(58) Field of Classification Search .................... 401/1, 401/2, 208, 213, 219, 220, 196
   See application file for complete search history.

(56) References Cited

U.S. PATENT DOCUMENTS

| 1,394,662 A | 10/1921 | Blomquist ..................... 401/1 |
| 1,831,463 A | 11/1931 | Nobbs ............................ 401/1 |
| 4,182,786 A | 1/1980 | Hertel ............................ 401/1 |
| 5,315,811 A | 5/1994 | Biesecker et al. ............. 53/474 |
| 6,273,625 B1 | 8/2001 | Martinez de San Vincente Oliveras ............................. 401/1 |

FOREIGN PATENT DOCUMENTS

| EP | 368 698 A2 | 5/1990 |
| EP | 560 594 A1 | 9/1993 |
| EP | 561 466 A1 | 9/1993 |
| EP | 813 828 A1 | 12/1997 |

(Continued)

OTHER PUBLICATIONS

Patent Abstract of Japan No. JP 59-29611 filed Feb. 16, 1984; Depilatory Wax Product and Method for Using the Same.

*Primary Examiner*—David J. Walczak
(74) *Attorney, Agent, or Firm*—Fish & Richardson P.C.

(57) ABSTRACT

A container adapted to heat and dispense material comprises a container (1) which defines a first compartment (3) adapted, in use, to be filled with the material requiring heating, such as epilatory wax, and a second compartment (9) adjacent to the first compartment and separated therefrom by a dividing wall (8). The container (1) has an inlet to the second compartment (9) in the outer wall thereof which is closeable by a plug or stopper (10). In use, the second compartment (9) is filled with a heated liquid, such as warm water, to heat the material in the first compartment (3), so that it can be applied to a site through an applicator (12).

10 Claims, 3 Drawing Sheets

FOREIGN PATENT DOCUMENTS

| | | |
|---|---|---|
| FR | 2 764 490 | 12/1998 |
| GB | 186769 | 10/1922 |
| GB | 337614 | 11/1930 |
| GB | 367395 | 2/1932 |
| GB | 660759 | 11/1951 |
| GB | 1 502 147 | 2/1978 |
| GB | 2 082 124 A | 3/1982 |
| GB | 2 182 762 A | 5/1987 |
| GB | 2 286 811 A | 8/1995 |
| GB | 2 321 443 A | 7/1998 |

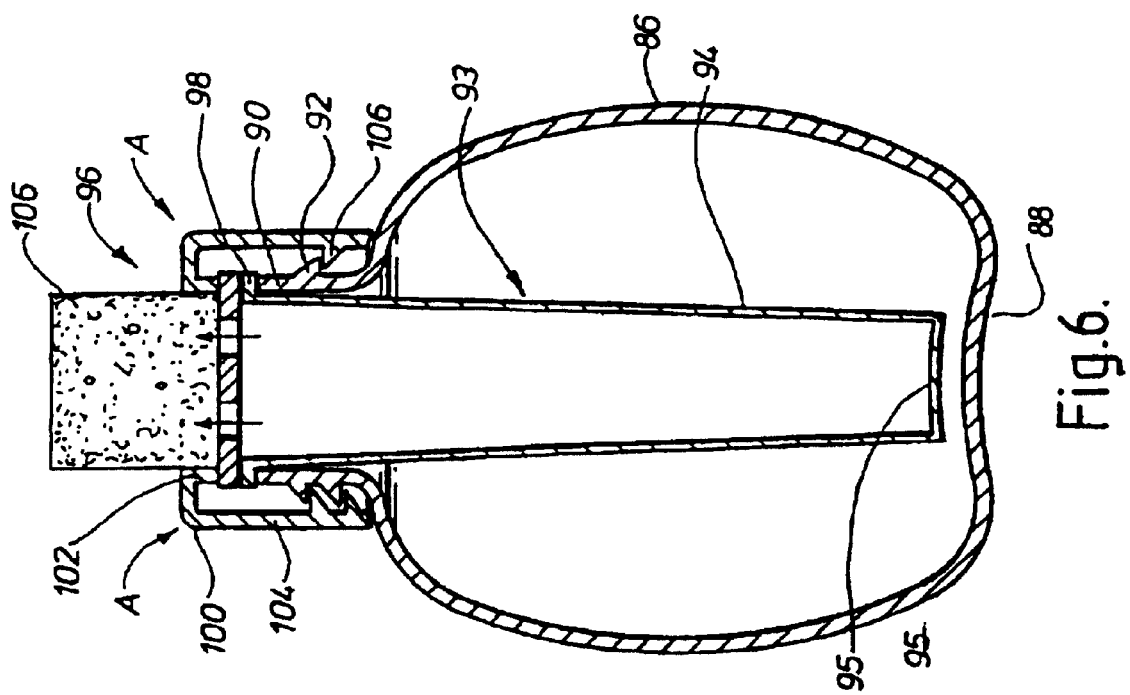
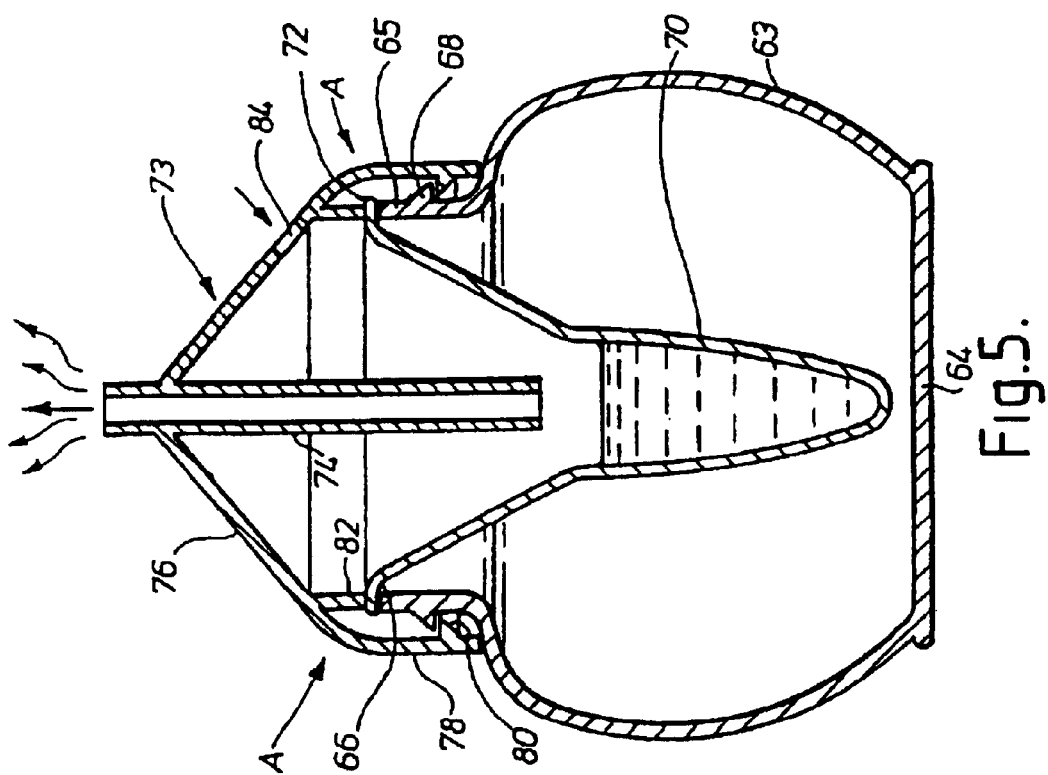

CONTAINER FOR DISPENSING A HEATED FLUID

CROSS REFERENCE TO RELATED APPLICATIONS

This is a division of application Ser. No. 09/937,050 filed on 20 Sep. 2001, now U.S. Pat. No. 6,616,363.

BACKGROUND OF THE INVENTION

The present invention relates to a container and, more particularly, to a container provided with integral means for facilitating warming of material inside it, prior to dispensing thereof.

It is known to provide epilatory wax in a bottle or container fitted with an applicator to allow direct application of the wax to the skin. However, the wax must be warmed before it can achieve sufficient viscosity to pass through the applicator and be spread on. One way of warming the wax is to stand the container in hot water. Another is to place the container in a microwave oven. Neither technique is entirely satisfactory.

Standing the container in hot water is relatively safe. The wax, which can burn at a temperature of above 57° C., is unlikely to be overheated provided that the water is not too hot. However, the container becomes wet which is messy and can make it difficult to handle. Moreover, a vessel to hold the hot water may not always be readily to hand.

Heating the wax in a microwave oven is not very satisfactory from a safety point of view. Great care must be taken to ensure that the wax is not overheated. This is not always easy as microwave ovens have a tendency to cause localised hot spots in the material being heated. Furthermore, the power output and efficiency of microwave ovens can vary significantly from one to another. It will be readily understood that it is undesirable to allow the possibility of overheating in any material which is to be applied directly to the skin.

It is an object of the present invention to provide a container provided with integral means for facilitating warming of its contents, thereby obviating or at least mitigating the problems described hereinabove.

SUMMARY OF THE INVENTION

According to the present invention, there is provided a container for heating material within it and for dispensing said material once heated, the container comprising:
(a) a first compartment for location of the material; and
(b) a second compartment for receiving a hot liquid, the second compartment being isolated from the first compartment such that liquid in the second compartment and material in the first compartment cannot mix, the second compartment being in thermal communication with the first compartment;
wherein the second compartment has an opening in the form of an inlet for the introduction of the hot liquid, the inlet having a removable closure; and
wherein the first compartment has an opening in the form of a restricted outlet adapted for prolonged dispensing of heated material, the outlet having a removable closure.

BRIEF DESCRIPTION OF THE DRAWINGS

FIG. 5 shows a sectional view of a further embodiment of a container according to the present invention; and FIG. 6 shows a sectional view of a further embodiment of a container according to the present invention.

DETAILED DISCLOSURE

Figure 1:
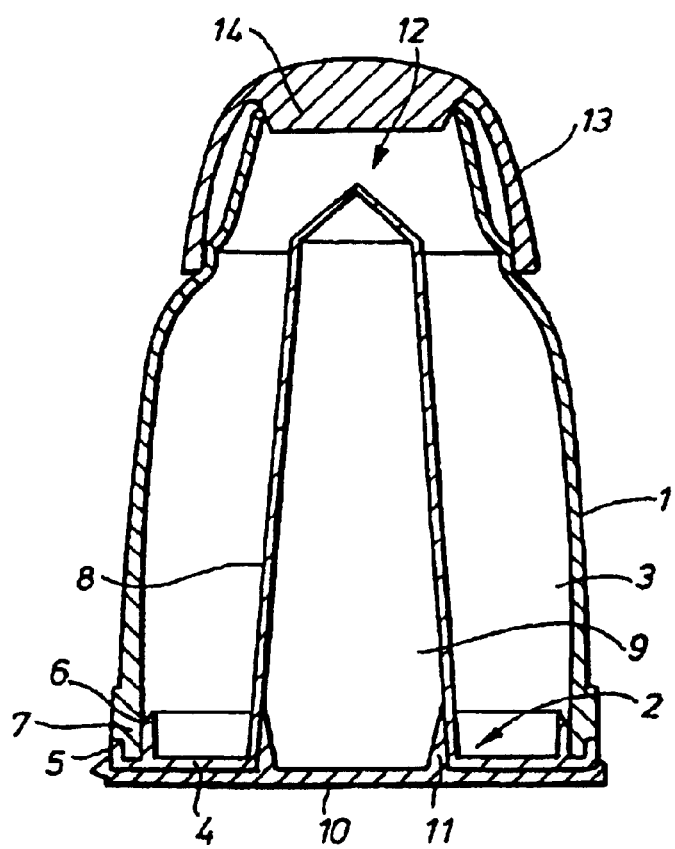
FIG. 1 shows a sectional view of one embodiment of a container according to the present invention.

The volume of the first compartment is preferably not so great, having regard to the volume of the second compartment, that the material in the first compartment cannot be heated to the particular extent required. Preferably, the ratio of the volume of the second compartment to the volume of the first compartment is at least 1:2, preferably at least 1:1.

The container of the present invention is intended for use with materials which need to be thermally modified by heating before use.

Examples of materials which need to be heated prior to use include personal or cosmetic materials such as epilatory waxes or facial masks; cleaning materials such as shoe or furniture waxes; pharmaceutical materials such as creams for the relief of joint pain; and volatile materials, for example containing an insecticide, or a deodorant, fragrance or other air freshener.

In one useful embodiment the first compartment may contain, in use, a volatile liquid which is to be evaporated.

In another, preferred, embodiment the first compartment may contain, in use, a solid or a viscous liquid (which terms together include pastes, waxy solids, semi-solids and gels) which is to be heated to provide a flowable liquid.

In an especially preferred embodiment the first compartment may contain, in use, an epilatory wax.

As used in the present specification, the term "wax" refers generally to any material which is used for the removal of hair from the body, and which is initially heated and is then applied to the body in a generally molten state, allowed substantially to solidify and be removed from the body with the unwanted hair. Thus, the term includes both true waxes and other materials suitable for epilation, such as compositions based on resins or compositions based on sugars, in particular glucose.

The hot liquid for thermally modifying the material is preferably hot water, for example from a hot tap or kettle. In order to warm the material, hot water is poured into the second compartment. Over a period of time the heat from the hot water transfuses to the material in the first compartment.

According to one aspect of the first embodiment of the present invention, a dividing wall extends between and is connected to the outer walls of the container, thereby dividing the container into two side-by-side or two end-to-end compartments.

According to another aspect of the first embodiment of the present invention, a dividing wall is in the form of a body which extends longitudinally into the container from the outer wall thereof, the interior of the body defining one of the first and second compartments, and the space between the outer surface of the body and the inner surface of the container forming the other.

Where the said first compartment is formed by the interior of the said body, preferably the end thereof connected to the outer wall of the container is provided with said opening to the compartment, and the opposite end is closed. Preferably the body is removable from the container. Preferably the act of removing the body from the container opens the opening to the other compartment. Thus, the body, which preferably constitutes the first compartment, may serve as the removable closure of the second compartment.

Conveniently, the container is comprised of a base, four side walls or one cylindrical side wall, and a top, and the said inlet to the body is at the top or the base of the container.

The restricted outlet may be in the form of an applicator adapted to apply a film of heated liquid material to a surface. The applicator may comprise a narrow elongate slot in the top or the base of the container through which the material can be expressed. Conveniently, the removable closure thereof is provided with a narrow elongate tongue on the inside thereof which engages in the slot to seal it. More preferably, the applicator may comprise a roller ball.

The applicator is preferably removable, thereby to permit removal of the first compartment so that, for example, it can be replaced by a refill.

Alternatively, the material could be removed from the device by means of a pump spray, trigger spray or automatic valve. An automatic valve, or even a simple opening, would be useful when the material is a material to be vaporized, for example an air freshener or an insecticide.

The material used to form the thermal communication between the first and second compartments is suitably a good conductor and is preferably a metal (for example aluminium). Alternatively it could be a plastics material, for example polyethylene. The material used to form the outer wall of the container is preferably a poor conductor and is preferably a ceramic material or a plastics material, for example polypropylene. A layer of thermal insulation may surround or be provided in the outer wall of the container.

Conveniently, heat sensitive means may be provided to indicate when the material in the first compartment has reached a desired temperature. For example a heat sensitive strip may be provided on or within the outer wall of the body defining the first compartment, the strip thereby indicating when the temperature of the material contained therein has reached the desired temperature.

In accordance with a second aspect of the present invention there is provided a container for heating material within it and for dispensing said material once heated, the container comprising:

(a) a first compartment containing the material, the material at ambient temperature being a solid or a liquid and at an elevated temperature being a liquid or a vapour (in the case of a solid at ambient temperature) or a less viscous liquid or a vapour (in the case of a liquid at ambient temperature);

(b) a second compartment for receiving a hot liquid, the second compartment being isolated from the first compartment such that the hot liquid and the material cannot mix, the second compartment being in thermal communication with the first compartment;

wherein the second compartment has an opening in the form of an inlet for the introduction of the hot liquid, the inlet having a removable closure; and wherein the first compartment has an opening in the form of a restricted outlet adapted for prolonged dispensing of the heated material within it, the outlet having a removable closure.

In accordance with a third aspect of the present invention there is provided a method of dispensing a heated material from a container as defined herein, containing hot water as the heating liquid in the second compartment.

In accordance with a further aspect of the present invention there is provided a kit comprising a container as defined herein and at least one refill of said material contained within a body which, when in use in the container, comprises the first compartment.

Embodiments of the present invention will now be described, by way of example, with reference to the accompanying drawings.

Referring to FIG. 1 of the accompanying drawings, there is shown a container comprising an outer wall 1 having an inverted, generally U-shaped cross-section; thus being of generally tubular shape. A layer of thermal insulation (not shown) may be provided in or surround outer wall 1. A heat-sensitive strip (not shown) may be provided on the outer wall 1. the circular bottom of the outer wall 1 is closed by a press-fitted closure member 2 to define a compartment 3. The closure member 2 comprises a first generally annular outer section 4 having a first locating member 5 at its edge and a second locating member 6 disposed radially inwardly of the first locating member. Both locating members 5 and 6 are annular and between them define a groove in which the free edge of the sidewall 7 of the outer wall 1 is received and secured. The closure member 2 also comprises an inner generally tubular section 8 which is open at the end adjoining the end remote therefrom. The inner section 8 extends into the compartment 3 and thereby forms of itself a second compartment 9 therein. The compartment 3 of the container is filled with material prior to fitting the closure member 2 to the outer wall 1. In order to accommodate the tubular inner section 8, the compartment 3 is only partially filled with material prior to the introduction of the tubular inner section.

The open end of the second compartment 9 is closed by a cap 10. The cap 10 is provided on its inwardly facing surface with annular locating means 11 which engages in the open end of the inner section 8 and forms a press fit therewith. The cap 10 covers the entire area of the bottom of the container and is flat, so that the container may be stood on it, in the orientation shown in FIG. 1.

A narrow elongate slot 12 is provided in the top of the outer wall 1 through which material contained in the compartment 3 can be expressed. To prevent unwanted expression of the material before or after use, the slot 12 is covered by a push on/pull off cap 13. The cap 13 has a tongue 14 which projects from the inner surface thereof to engage in the slot 12 and close the same.

In use, the outer compartment 3 contains a material, typically epilatory wax, which must be warmed through before use. In the case of epilatory wax it must be warmed through so that it can achieve the required viscosity to be applied to the user's skin.

In order to warm the material, the cap 10 is removed to open the inlet to the inner compartment 9. The inner compartment 9 is then filled with hot water and the cap 10 replaced. Over a period, of time heat from the hot water in the inner compartment 9 transfuses through the wall of the inner section 8 to warm the wax in the outer compartment 3. Once the wax has achieved the required temperature and attained a sufficient viscosity, it then can be expressed through the slot 12 onto the user's skin.

Figure 2:
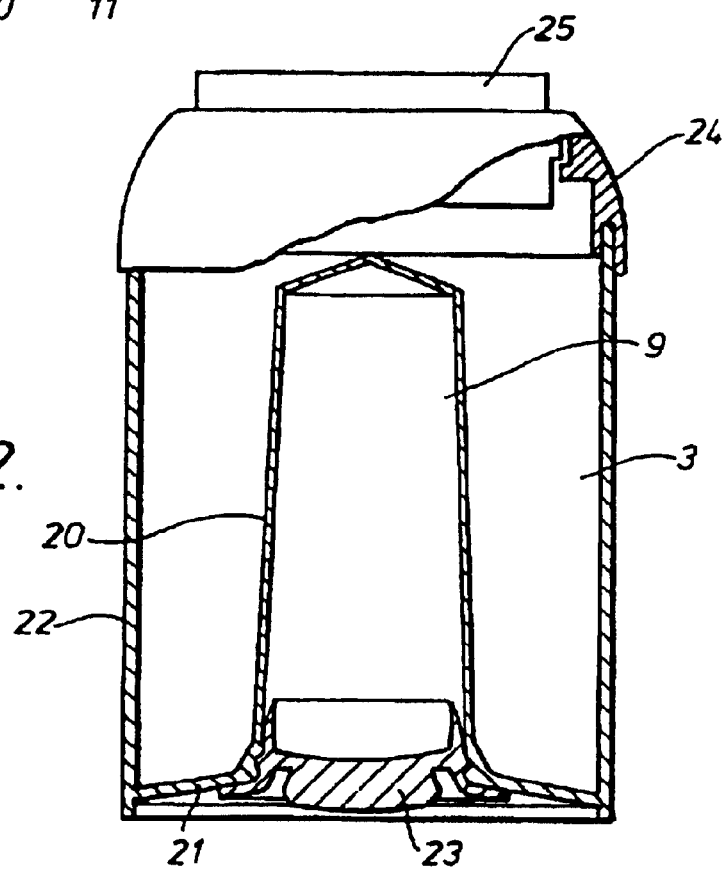
FIG. 2 shows a sectional view of another embodiment of a container according to the present invention.

Referring now to FIG. 2 of the accompanying drawings, there is shown another container according to the present invention. In its essential respects this embodiment is identical to the embodiment described hereinabove with reference to FIG. 1. In this regard, it comprises an outer compartment 3 which is adapted in use to be filled with material, and an inner compartment 9 which is adapted, in use, to be filled with hot water to warm the material in the outer compartment 3.

In the embodiment of FIG. 2, the inner compartment 9 is formed by moulding an inwardly extending tubular section 20 into the base 21 of a vessel-shaped component 22. The tubular section 20 is open at the end thereof adjoining the base 21 and closed at the end which is remote therefrom. A removable cap 23 is provided to allow the inner compartment 9 formed by the tubular section 20 to be closed.

The upper, open end of the vessel-shaped component 22 is closed by a closure member 24. As shown in the drawing, the closure member 24 is provided with an aperture within which is mounted a cylindrical roller 25 to facilitate application of the material contained within the outer compartment 3 to a surface. However, it will be understood that the cylindrical roller 25 can be replaced by a single elongate narrow slot in the manner as described hereinabove with reference to FIG. 1, or by a ball roller.

It will be understood that, in the manufacture of the embodiment of FIG. 2, the container is filled with material through the open top end of the vessel-shaped component 22 with the closure member 24 removed. Once filled, the closure member 24 is put in place, for example by snap fitting.

Figure 3:
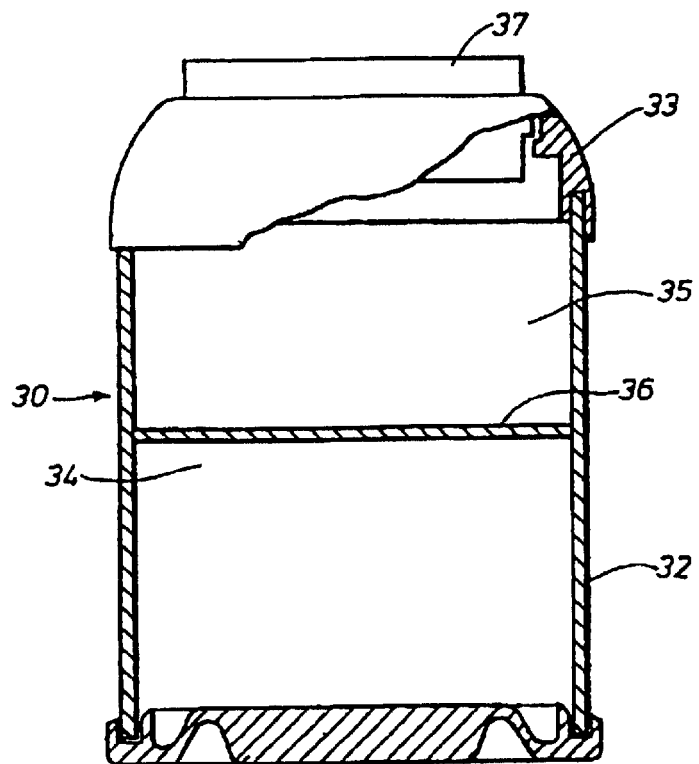
FIG. 3 shows a sectional view of yet another embodiment of a container according to the present invention.

Referring now to FIG. 3, there is shown yet another container 30 embodying the present invention, consisting of a base 31, side walls 32 and a top 33; the base, side walls and top together defining a generally cuboid-shaped container. The container 30 is divided into two separate compartments 34 and 35 by a dividing wall 36. The dividing wall 36 is connected to and extends between the side walls 32 of the container.

An applicator in the form of a cylindrical roller 37, identical to that shown in the embodiment of FIG. 2, is mounted in the top 33 of the container 30. The upper compartment 35 is filled with material prior to fitting the top 33.

In use, the base 31 is removed and the lower compartment 34 is filled with hot water. The base is then snap-fitted back onto the side walls of the compartment 34. Alternatively, the base 31 may be provided with a removable stopper (not shown) for the purpose of filling the compartment 34 with hot water. Heat from the hot water transfuses through the dividing wall 36 to warm the material in the compartment 35. Once the material has been warmed sufficiently, it can be used.

Figure 4:
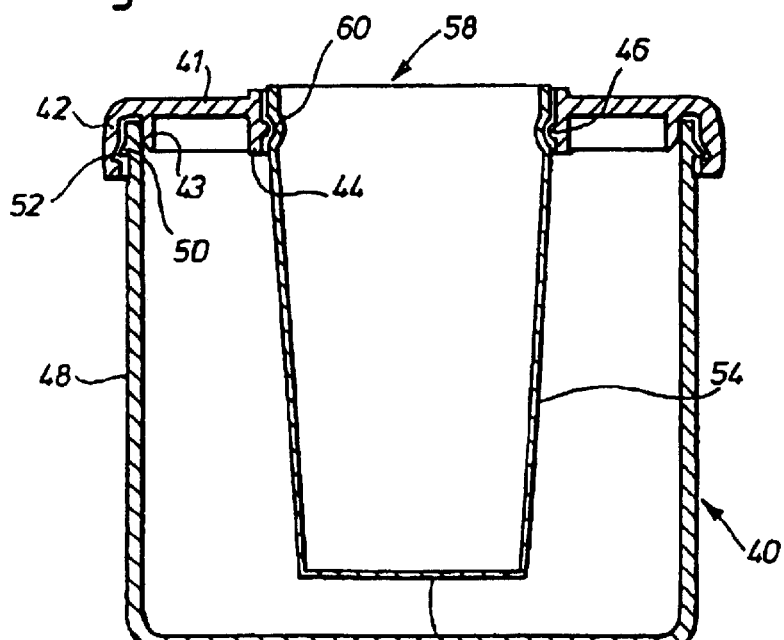
FIG. 4 shows a sectional view of a further embodiment of a container according to the present invention.

Referring to FIG. 4 of the accompanying drawings, there is shown an alternative embodiment of the invention comprising a generally cylindrical container 40. The container 40 is provided with a top wall 41 having a circular central opening. The top wall 41 has an outer downwardly depending skirt 42, extending around its periphery, a downwardly depending rib 43 slightly inwardly spaced from the skirt 42, and an inner downwardly depending skirt 44 around the central opening. On the inner cylindrical face of the inner skirt there is an annular rib 46. The upper region of the side wall 48 of the container has, facing outwards, an annular projection 50 and the skirt 42 has, facing inwards, a complementary annular groove 52. Thus, the top wall 41 may be snap-fitted onto the side wall 48 of the container, with the top of the side wall engaged between the skirt 42 and the rib 43, and with the projection 50 and groove 52 interengaged.

A body 54 of generally cylindrical shape is also provided. The body 54 is closed at end 56. For clarity it is shown open at the top 58 but in practice would be closed by a suitable applicator, for example a roller ball. In use, the body 54 will contain a material which is to be heated, for example an epilatory wax. Adjacent the upper rim of the body 54 is an outwardly facing annular groove 60 which is adapted to engage with the inwardly facing annular rib 46 formed on the inner skirt.

In use, the container 40 is partly filled with hot water. The body 54 containing the material is then snap-fitted into the container by means of the engagement of the groove 60 of the body 54 and the rib 46 of the inner skirt; the body 54 is then one compartment of the container, and the remaining volume of the container 40 is the other compartment. Using this arrangement, it is possible to provide refills of the material contained in body 54 for use with a single container 40. The refills may be provided with a roller ball fitted or may be supplied without one, the roller ball mechanism itself being removable from the previous refill, now empty, to be fitted to the next refill.

FIG. 5 shows a container having a lower vessel 63 of somewhat bulbous shape, having a flat bottom 64, and an upper neck 65, ending in a wide mouth 66. On its outer face, the neck 65 has an annular rib 68.

Suspended within the vessel is an inner compartment 70, upwardly open, which contains a material to be dispensed by evaporation. The inner compartment widens in the upward direction from a closed or blind bottom wall, and it terminates in an annular flange 72. The flange 72 is of size such that it rests on the rim forming the mouth 66.

The third part of the container is a press-on closure part 73. The closure part 73 has a central narrow tubular portion 74 whose lower end is close to the surface of the material which is to be evaporated, at the commencement of evaporation. The upper end of the tubular portion 74 is the highest part of the container and the point at which vapour leaves the container. Slightly below that point extends a conical portion 76 of the closure part. At its lower region the closure part 76 is provided with two formations, namely an outer skirt 78 formed on its inner surface with an annular rib 80 which can slide past rib 68 to secure the closure part 73 over the mouth of the lower part of the container; and, inboard of the skirt 78, a shorter skirt 82 aligned with the rim forming the mouth 66 of the vessel, the skirt 82 and rim 66 entrapping between them the flange 72 of the inner compartment.

The conical portion 76 is provided with a circular vent 84.

When the container is assembled the aforesaid second compartment is the volume between the vessel and the inner, first compartment.

In use, to start or accelerate the evaporation of the volatile material within the inner compartment 70, the closure part 73 is first removed. This may be achieved by pressing the closure part in the direction of the arrows A, thereby to splay the skirt 78 and disengage the rib 80 from the rib 68. The closure part may then be lifted out of the vessel. The inner compartment may then be lifted out and hot water, for example from a hot tap or kettle, may be poured into the vessel, up to a marked level which is near but not in the neck 65. The inner compartment 70 is then replaced and the closure part pressed on. Evaporation of the volatile material is accelerated as it becomes warm and it will leave the container as a vapour mainly through the tubular part 74.

Once the volatile material has been exhausted by evaporation the inner container may be replaced by a refill.

The volatile material may, for example, be an air freshener and/or an insecticide.

Closure members, for example simple stoppers, may be provided to block the tubular member and the vent 84, should it be wished to interrupt emission of the volatile material.

In another embodiment, not shown in the drawings, a device of the type shown in FIG. 5 is employed, but the tubular member and the vent each have a valve. The valve in the tubular member may be a one-way valve openable in the outflow direction and the vent may have a one-way valve openable in the inflow direction.

FIG. 6 shows a re-fillable container adapted to dispense a polish, for example a shoe polish or a furniture polish. Like the embodiment of FIG. 5, the container comprises a main vessel 86 having a base 88 on which the container may be stood, and, at its upper end, a neck 90, having an outwardly-facing annular rib 92. The second part is the inner compartment 93, having a generally tubular wall portion 94, a blind bottom wall 95 and an applicator head 96 at its top end. The upper end of the tubular portion terminates in an outward annular flange 98. The third part is a securement cap 100 having an inner annular wall 102 aligned with the neck 90 and adapted to entrap, with the neck 90, the flange 98; and an outer skirt 104, extending considerably below the skirt 102, and having an inwardly-directed rib 106 adapted to engage with the rib 92.

In this embodiment, the material in the inner container is, at ambient temperature, a waxy or pasty solid, and at a somewhat raised temperature becomes a flowable liquid. The applicator head 96 comprises an open-cell foam 106.

The device of FIG. 6 is used in the manner of the device of FIG. 5. The securement cap 100 is removed by squeezing in the direction of the arrows A. The inner compartment 92 is removed and hot water is poured into the outer vessel 86, up to a mark. The inner container is replaced and the cap put onto secure it in place. The arrangement is such that the water does not leak from the container even when the container is inverted for application of the polish.

In other embodiments, a brush could be used, instead of the sponge 106.

It will be readily apparent that a container of the present invention allows a material contained therein to be warmed through very easily. One compartment thereof can be filled with hot water, for example from a tap in the user's kitchen or bathroom, creating little or no mess. Significantly, there is little or no risk to the user of the material becoming too hot for safe use as is the case with materials heated in a microwave oven.

The invention claimed is:

1. A container for heating material within it and for dispensing said material once heated, the container comprising:
    (a) a first compartment for location of the material, and
    (b) a second compartment for receiving a hot liquid, the second compartment being isolated from the first compartment such that liquid in the second compartment and material in the first compartment cannot mix; the second compartment being in thermal communication with the first compartment;
    wherein the second compartment has an inlet for the introduction of the hot liquid, the inlet having a removable closure; and
    wherein the first compartment has a restricted outlet in the form of an applicator for prolonged dispensing of heated liquid material in the container, the applicator being adapted to apply a film of the material to a surface, the outlet having a removable closure.

2. A container as claimed in claim 1, wherein the first and second compartments are separated by a dividing wall.

3. A container according to claim 2, wherein the dividing wall is in the form of a body which extends longitudinally into the container from the outer wall thereof, the interior of the body defining one of the first and second compartments, and the space between the outer surface of the body and the inner surface of the container defining the other compartment.

4. A container according to claims 1 or 3 wherein the applicator comprises a narrow elongate slot through which the heated liquid material can be expressed.

5. A container according to claims 1 or 3, wherein the applicator comprises a roller or roller ball.

6. A container according to claim 1, wherein a layer of thermal insulation surrounds or is provided in the outer wall of the container.

7. A container according to claim 1, which additionally comprises, heat indication means to indicate when the temperature of the material in the first compartment has reached a desired temperature.

8. A container for heating material within it and for dispensing said material once heated, the container comprising:
    (a) a first compartment containing the material, the material at ambient temperature being a solid or a liquid and at an elevated temperature being a liquid or a vapour (in the case of a solid at ambient temperature) or a less viscous liquid or a vapour (in the case of a liquid at ambient temperature);
    (b) a second compartment for receiving a hot liquid, the second compartment being isolated from the first compartment such that the hot liquid and the material cannot mix, the second compartment being in thermal communication with the first compartment;
    wherein the second compartment has an inlet for the introduction of the hot liquid, the inlet having a removable closure; and
    wherein the first compartment has a restricted outlet adapted for prolonged dispensing of the heated material within it, said outlet having a removable closure.

9. A container according to claim 8 wherein the first compartment contains epilatory wax.

10. A method of dispensing heated material from a container as claimed in claims 8 or 9, comprising the steps of: introducing hot water into the second compartment; closing the inlet thereof using its closure; and permitting or causing the heated material within the first compartment to be dispensed through the restricted outlet.

* * * * *